(12) United States Patent
Vafi et al.

(10) Patent No.: US 6,259,098 B1
(45) Date of Patent: Jul. 10, 2001

(54) LOW COST, LOW RESOLUTION INTERCONNECT FOR A SOLID-STATE X-RAY DETECTOR

(75) Inventors: Habib Vafi, Waukesha; Scott W. Petrick, Sussex, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/313,530

(22) Filed: May 17, 1999

(51) Int. Cl.[7] ..................................................... G01T 1/00
(52) U.S. Cl. ..................................... 250/370.09; 378/98.8
(58) Field of Search ....................... 250/370.09; 378/98.8; 348/162

(56) References Cited

U.S. PATENT DOCUMENTS

| | | | |
|---|---|---|---|
| 4,161,655 | * 7/1979 | Cotic et al. | 250/385.1 |
| 5,822,392 | * 10/1998 | Hedengren | 378/98.8 |
| 5,896,173 | 4/1999 | Hassler | 348/162 |
| 5,974,109 | * 10/1999 | Hsieh | 378/19 |
| 6,081,576 | * 8/2000 | Schanen et al. | 378/19 |
| 6,091,795 | * 7/2000 | Schafer et al. | 378/19 |
| 6,115,448 | * 9/2000 | Hoffman | 378/19 |
| B1 6,173,031 | * 1/2001 | Hoffman et al. | 378/19 |

* cited by examiner

Primary Examiner—Robert H. Kim
Assistant Examiner—Allen C. Ho
(74) Attorney, Agent, or Firm—Armstrong Teasdale LLP; Christian G. Cabou

(57) ABSTRACT

The present invention, in one form, is a flexible interconnect circuit for altering the resolution of an imaging system. In one embodiment, by combining a plurality of detector array signal lines within the interconnect circuit, the imaging system resolution is altered. Each interconnect circuit includes a plurality of contacts at a first end and a second end and a plurality of conductors extending therebetween electrically connected to at least one contact at each end. By altering the number of contacts which are connected together, the resolution of the imaging system is altered.

29 Claims, 4 Drawing Sheets

LOW RESOLUTION

HIGH RESOLUTION

LOW RESOLUTION

LOW COST, LOW RESOLUTION INTERCONNECT FOR A SOLID-STATE X-RAY DETECTOR

BACKGROUND OF THE INVENTION

This invention relates generally to x-ray diagnostic medical imaging and more particularly, to a flexible interconnection circuit for altering the resolution of an imaging system.

In many x-ray imaging system configurations, an x-ray source projects an area beam which is collimated to pass through a region of interest of the object being imaged, such as a patient. The beam, after being attenuated by the object, impinges upon an array of radiation detectors. The intensity of the radiation beam received at the detector array is dependent upon the attenuation of the x-ray beam by the object. Each detector element, or pixel, of the array produces a separate electrical signal that is a measurement of the beam attenuation at that location of the detector. The attenuation measurements from all the detector pixels are acquired separately to produce a transmission profile.

Due to the many different imaging requirements, multiple versions or configurations of x-ray systems must be developed, manufactured and supported in the field. More specifically, for a high resolution x-ray system, a high resolution detector array must be designed, tested and fabricated. In addition, a data acquisition system (DAS) must be designed, tested and fabricated to sample the large number of signals generated by the high resolution detector array. Additionally, unique interconnect cables must be developed to transfer the signals between the detector array and the DAS. In order to fabricate an x-ray system having a lower resolution, at least one known system utilizes a separately designed detector array having a lower resolution, DAS having fewer channels, and interconnect cable connecting each detector array line to each DAS channel. AS a result of the different configurations of the components, design costs and risks are increased. In addition, manufacturing and field support must be familiar with each configuration as well as stock inventory of each component.

It would be desirable to provide an imaging system which minimizes the umber of components which must be changed to alter the resolution of the system. It would also be desirable to provide a flexible interconnect circuit which allows the resolution of the imaging system to be quickly and inexpensively modified.

BRIEF SUMMARY OF THE INVENTION

These and other objects may be attained by a flexible interconnect connection which, in one embodiment, alters the resolution of an imaging system by combining detector array signal lines. Particularly, the flexible interconnect cable includes a plurality of first end contacts, a plurality of second end contacts and a plurality of conductors extending between the first end contacts and the second end contacts. By altering the configuration of the flexible interconnect cable, the resolution of the imaging system is altered. More specifically, while utilizing a common detector array and common DAS components, the resolution of the imaging system is altered by electrically combining different numbers of detector array signals lines to each DAS channel.

In one embodiment, where the detector array includes M×N pixels, the physical dimensions of at least a portion of the first end contacts are modified so that two output data lines from the detector array are electrically connected to each DAS channel so that the resolution of the system is reduced to M/2 by N. As a result of altering only the flexible interconnect circuit, a common detector array and common DAS module design may be utilized, thereby reducing the number of components which must be designed, fabricated, and field supported. In addition, where the DAS includes a plurality of modules, the number of modules may be reduced as a result of the reduced number of detector array signals.

The above described imaging system minimizes the number of components which must be modified to alter the resolution of the imaging system. In addition, the above described flexible interconnect cable enables the resolution of the imaging system to be quickly and inexpensively modified.

DETAILED DESCRIPTION OF THE INVENTION

Figure 1:
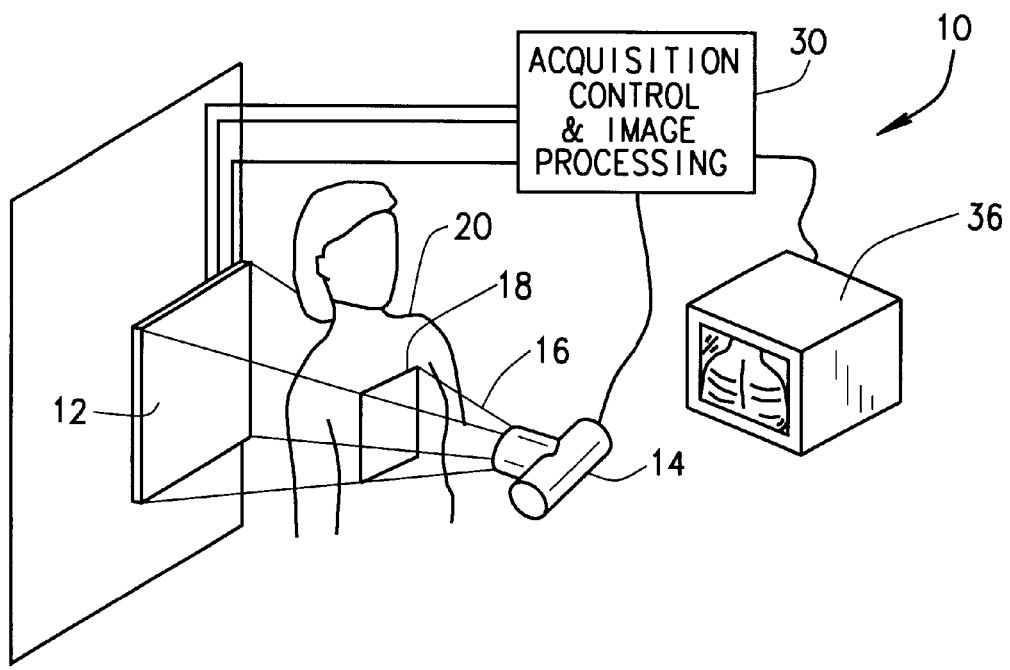
FIG. 1, pictorial view of an imaging system.

Referring to FIG. 1, an imaging system 10, for example, an x-ray imaging system, is shown as including a detector array 12 and an x-ray source 14 collimated to provide an area x-ray beam 16 passing through an area 18 of a patient 20. Beam 16 is attenuated by an internal structure (not shown) of patient 20 to then be received by detector array 12 which extends generally over an area in a plane perpendicular to the axis of the x-ray beam 16.

In one embodiment, detector array 12 is fabricated in a solid-state panel configuration having a plurality of detector elements, or pixels (not shown in FIG. 1) arranged in columns and rows. As will be understood to those of ordinary skill in the art, the orientation of the columns and rows is arbitrary; however, for clarity of description, it will be assumed that the rows extend horizontally and the columns extend vertically. Each pixel includes a photosensor, such as a photodiode, that is coupled via a switching transistor to two separate address lines, a scan line and a data line (not shown in FIG. 1). The radiation incident on a scintillator material (not shown) and the pixel photosensors measure, by way of change in the charge across the photodiode, the amount of light generated by x-ray interaction with the scintillator. As a result, each pixel produces an electrical signal that represents the intensity, after attenuation of patient 20, of an impinging x-ray beam 16. In one embodiment, detector array 12 is approximately 40 cm wide (x-axis) by 40 cm in height (z-axis). Of course, in other embodiments, the size of detector array 12 may be altered for the specific system requirements.

System 10 also includes an acquisition control and image processing circuit 30 which is electrically connected to x-ray source 14 and detector array 12. More specifically, circuit 30 controls x-ray source 14, turning it on and off and controlling the tube current and thus the fluence of x-rays in beam 16 and/or the tube voltage and thereby altering the energy of the x-rays in beam 16. In one embodiment, acquisition control and image processing circuit 30 includes a data acquisition system (DAS) 32 having at least one DAS module, or circuit (not shown in FIG. 1), which samples data from detector array 12 and transmits the data signals for subsequent processing. In one embodiment, each DAS module includes a plurality of driver channels or a plurality of read out channels. Acquisition control and image processing circuit 30 receives sampled x-ray data from DAS 32 and generates an image and displays the image on a monitor, or cathode ray tube display 36 based on the data provided by each pixel.

Figure 2:
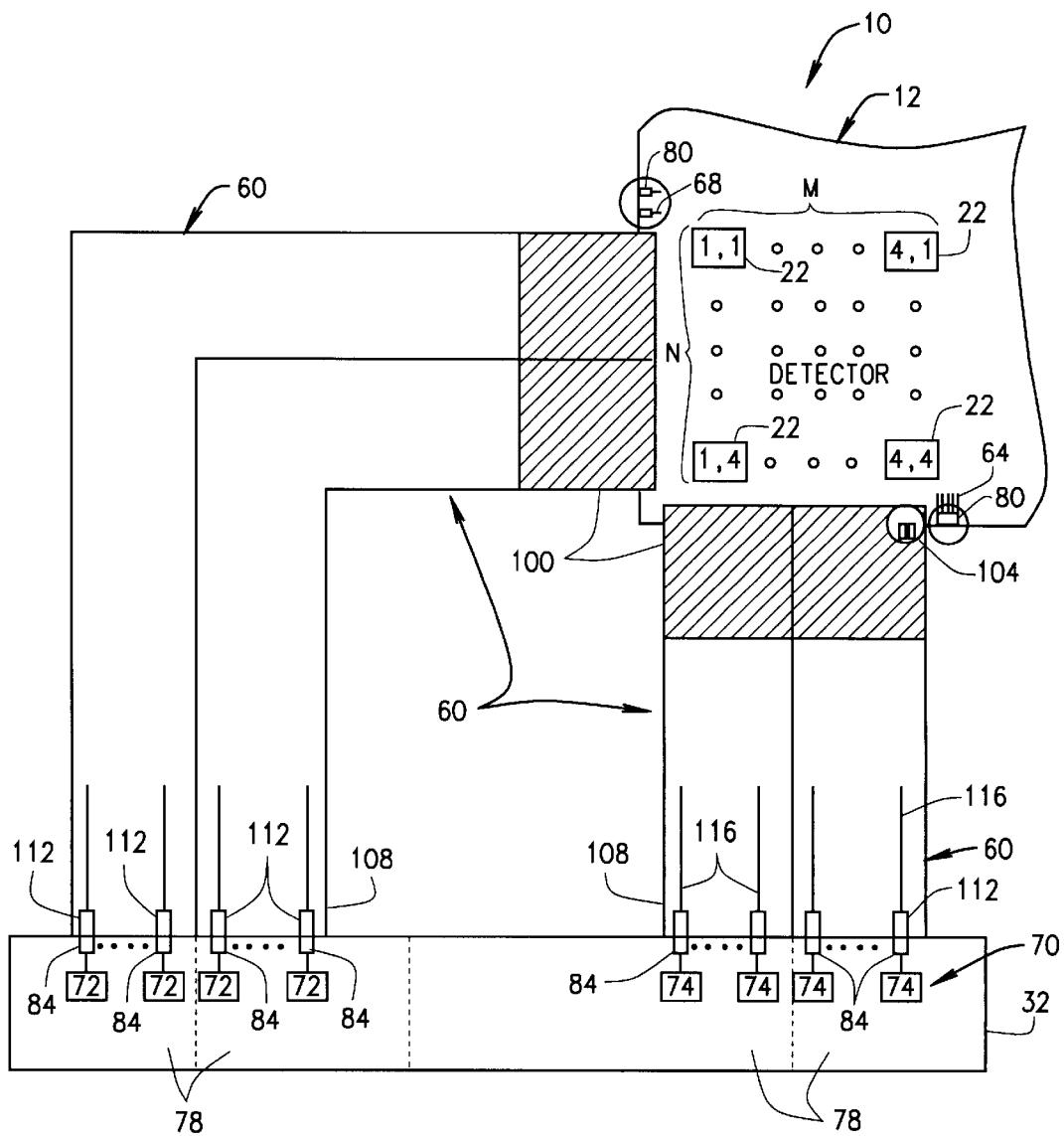
FIG. 2 is a high resolution configuration of the imaging system of FIG. 1.

As shown in FIG. 2, detector array 12 includes an array of individual sensing elements or pixels 22. Detector array 12 is electrically coupled or connected to DAS 32 utilizing at least one interconnect circuit, or cable 60. In one embodiment, interconnect circuit 60 is a flexible interconnect circuit. A signal electrode, or data line 64 of each pixel 22 is electrically connected to that of all the pixels 22 along one axis, or column. A signal from each data line 64 is measured separately from the other pixels 22 connected to the same data line 64 as a result of each pixel 22 in array 12 being separately controlled by a control electrode, or scan line 68 which is along an axis orthogonal to data line 64, e.g., row. For a detector array 12 having M data lines 64 and N scan lines 68, detector array 12 has M×N pixels 22.

As described above, detector array 12 transmits signals to DAS 32 which samples data from detector array 12 and transmits conversion results for subsequent processing. In one embodiment, DAS 32 includes a plurality of channels 70 including a plurality of driver channels 72 and a plurality of read out channels 74 for transmitting and sampling data from detector array 12. More specifically and in one embodiment, DAS 32 includes a plurality of modules 78 so that a total number of driver channels 72 is equal to the total number of scan lines 68 and a total number of read out channels 74 is equal to the total number of data lines 64. For example, where detector array 12 includes M×N pixels 22 each read out module 78 includes K read out channels 74 and each driver module includes L driver channels 72, DAS 32 includes M/K read out modules 78 and N/L driver modules 78. Of course, in other embodiments, each module 78 may include all driver channels 72, all read out channels 74, or any combination of driver channels 72 and read out channels 74.

Data from detector array 12 is generated by activating, or enabling, each scan line 68 and simultaneously measuring, or sampling, each data line 64. More specifically and during a scan, upon the activation of a single scan line 68 by a DAS driver channel 72, data is transmitted from each of the data lines 64 through cable 60 to each DAS read out channel 74. This process is repeated for each scan line 68 until data is transmitted for each pixel 22.

For example, where detector array 12 includes M by N pixels, and M and N each equal four, upon activation of the first scan line 68 (N=1), data is transferred from each of the M data lines 64 (elements 1,1; 2,1; 3,1; and 4,1) to DAS 32 via cable 60. Upon activation of the second scan line 68 (N=2), data is transferred from each of the M data lines 64 for the second scan line (elements 1,2; 2,2; 3,2; and 4,2) to DAS 32 via cable 60. This process is then repeated for each of the N scan lines 68 so data is transferred for each pixel, or element 22.

Figure 3:
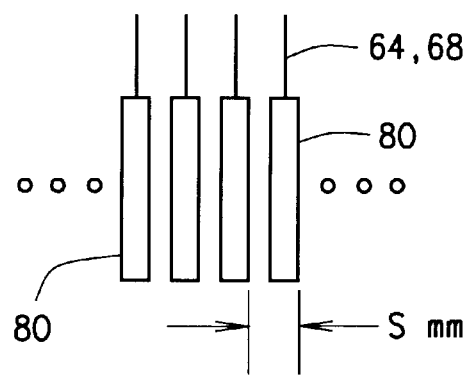
FIG. 3. represents the contact pitch of a flexible interconnect cable.

In one embodiment and as shown in FIG. 2, system 10 is configured as a "high resolution" system and includes a "high resolution" detector array 12, a "high resolution" DAS 32 and at least one high resolution cable 60. More specifically, high resolution detector 12 includes M data lines 64 and N scan lines 68. Each signal line (not shown) of detector array 12 is coupled, or electrically connected, to a detector array contact 80. More particularly and in one embodiment shown in FIGS. 2 and 3, each data line 64 and each scan line 68 of detector array 12 is coupled to a contact 80 having a pitch of S mm.

Referring again to FIG. 2 and in one embodiment, "High resolution" DAS 32 includes a plurality of modules 78 having a plurality of channels 70 including a total of M read out channels 74 and N driver channels 72. Each read out channel 74 and each driver channel 72 is electrically connected, or coupled, to a module contact 84.

DAS 32 and detector array 12 are electrically connected utilizing at least one cable 60. More specifically, each cable 60 includes a first end 100 having a plurality of contacts 104, a second end 108 having a plurality of contacts 112, and a plurality of electrical conductors 116 extending therebetween. First end 100 of cable 60 is coupled to detector array 12 and second end 108 is coupled to DAS 32. More specifically and in the "high resolution" configuration of system 10, each conductor 116 of cable 60 is electrically connected to one first end contact 104 and one second end contact 108 so that each driver channel 72 is electrically connected to one scan line 68 and each read out channel 74 is electrically connected to one data line 64. More specifically, an electrical path exists between each scan line 68 or data line 64 via each first contact 104 being electrically connected to a detector array contact 80 and each second end contact 112 being electrically connected to a DAS channel 70 via a module contact 84. In one embodiment, each DAS module 78 is electrically connected to detector array 12 utilizing a separate cable 60.

Figure 4:
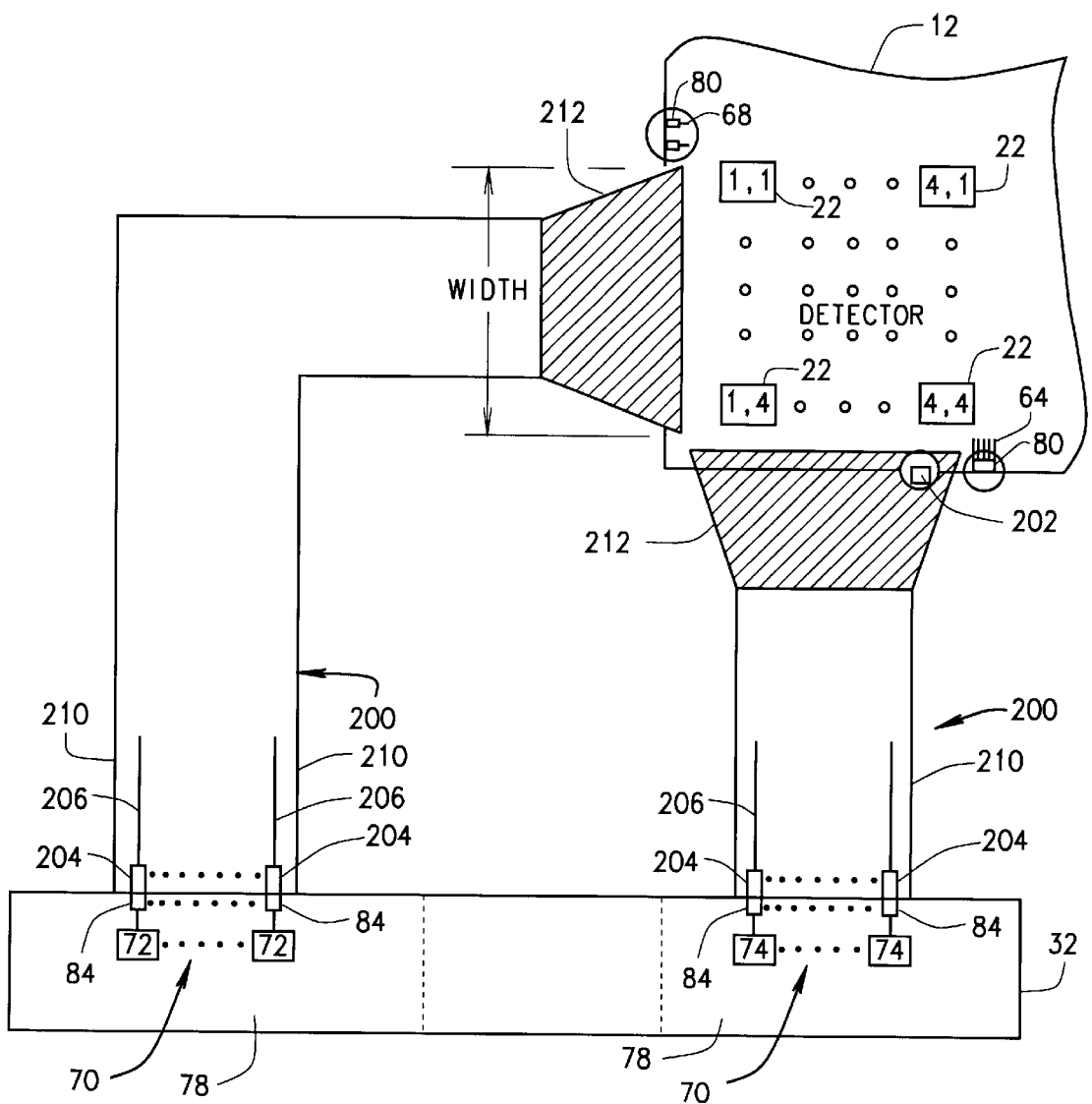
FIG. 4 is a low resolution configuration of the imaging system of FIG.

The resolution of system 10 is altered from the "high resolution" configuration to a "low resolution" configuration by altering the configuration of cable 60. Specifically and in one embodiment, as shown in FIG. 4 cable 60 is removed and at least one flexible interconnect circuit 200 is electrically connected to detector array 12 and DAS 32. Circuit 200, in one embodiment, includes a plurality of first end contacts 202, a plurality of second end contacts 204 and a plurality of electrical conductors 206 extending therebetween. Circuit 200 is configured to electrically connect a plurality of detector array signal lines (not shown) to each DAS channel 70.

Figure 5:
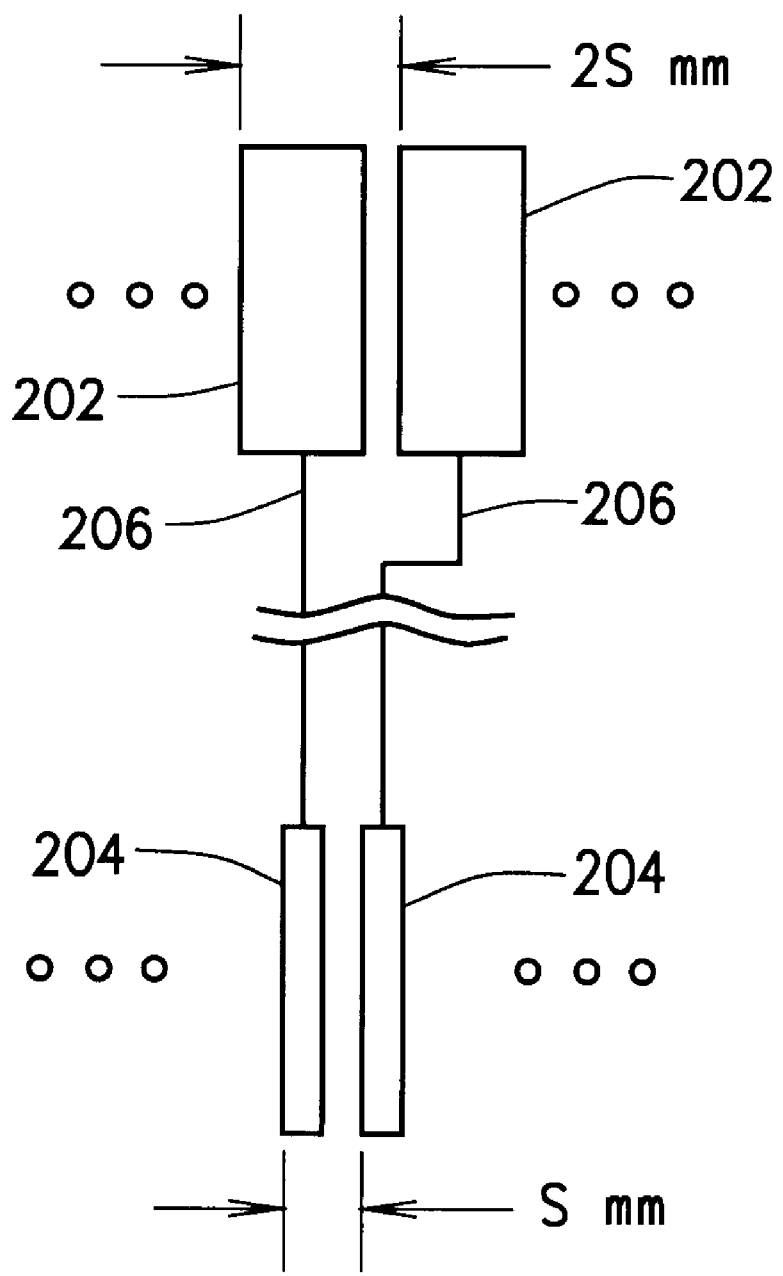
FIG. 5 is a alternative embodiment of contact pitch shown in FIG. 3.

Specifically and in one embodiment, circuit 200 is configured to electrically connect a plurality of scan lines 68 to each DAS driver channel 72 to reduce the resolution of system 10. More specifically, where detector array 12 includes M×N pixels 22, each contact 202 utilized to transfer data from driver channels 72 to detector array 12 is configured so that at least two scan lines 68 are electrically connected to each driver channel 72. For example and as shown in FIG. 5, where each detector array signal line contact 80 has a pitch of S mm, those contacts 202 utilized to transfer data from driver channels 72 to detector array 12 have a pitch of 2S mm so that each contact 202 is electrically connected to two detector array contacts 80. Those contacts 202 used to transfer data from detector array 12 to read out channels 74 of DAS 32 electrically connect each data line 64 to each read out channel 74. More specifically, each data line 64 is electrically connected to a single read out channel 74 via an electrical path including contact 202, a single conductor 206, a second contact 204 and a contact 84. As a result, the "effective" resolution of detector array 12 is reduced to M×N/2.

In one embodiment, due to the reduced number of signals coupled to DAS 32 and the number of second end contacts 204, the number of conductors 206 may be reduced as well as the number of second end contacts 204. In one embodiment and as shown in FIG. 4, where a second end 210 of cable 200 is configured to be the same physical size and be electrically connected to the same number of module contacts 84 as cable 60, a first end 212 of cable 200 is configured to be electrically connected to twice the number of detector contacts 80 and be twice the physical size, e.g., width, as each first end 100 of cable 60. In addition, where DAS 32 includes a plurality of modules 78, as a result of the reduced number of signals, due to the combination of detector data lines 64 and/or scan lines 68, the number of modules 78 may be reduced.

For example, utilizing an M×N detector array 12, a DAS 32 having four modules 78 and four cables 60, two cables 60 used for scan lines 68 and two cables 60 used for data lines 64, the resolution of system 10 is reduced from M ×N to M×N/2 by replacing cables 60 with flexible interconnect circuits 200 which electrically connects two scan lines 68 to each driver channel 72. As a result, the required number of modules 78 is reduced by a factor of up to two depending upon the configuration of each module 78. More specifically and in one embodiment, the number of driver channels is reduced by a factor of two. In other embodiments, circuit 200 is configured to electrically connect 3, 4 or T scan lines 68 so that the effective resolution of system 10 is reduced by a factor of 3, 4, or T, e.g., N/3, N/4, or N/T respectively.

In another embodiment, contacts 202 utilized to transfer data from data lines 64 to DAS 32 are configured so that at least two data lines 64 are electrically connected to each read out channel 74. As described above and similar to FIG. 5, the pitch of contacts 202 are altered so that each contact 202 is electrically connected to at least two read out channels 74. Each of the remaining contacts 202 are electrically connected to a scan line 68. As a result of replacing cables 60 with circuits 200, the resolution of system 10 is reduced.

For example, utilizing a M×N detector array 12, a DAS 32 having four modules 78 and four cables 60, two cables 60 used for scan lines 68 and two cables 60 used for data lines 64, the resolution of system 10 is reduced from M ×N to M/2×N by replacing two cables 60 with flexible interconnect circuit 200 which electrically connects two data lines 64 to each read out channel 74. In addition, the number of modules 78 required is reduced by a factor of up to two depending upon the configuration of each module 78. More specifically and in one embodiment, the number of read out channels 74 is reduced by a factor of two. As a result, the "effective" resolution of detector array 12 is reduced to M/2×N. Similarly, circuit 200 may be configured to electrically connect 3, 4 or V data lines 64 so that the resolution of system 10 is reduced by 3, 4, or V, e.g., M/3, M/4, or M/V, respectively.

In other embodiments, the resolution of system 10 may be altered by electrically connecting a plurality of data lines 64 to each read out channel 74 and electrically connecting a plurality of scan lines 68 to each drive r channel 72. More specifically, where circuit 200 electrically connects T scan lines 68 and V data lines 64, the resolution of system 10 is reduced to M/V×N/T, where the values of V and T each are any positive integer.

In another embodiment, circuit 200 alters the resolution of system 10 by electrically connecting a plurality of conductors 206 together so that a plurality of detector array lines are electrically connected. More specifically, and in one embodiment at least two conductors 206, each connected to a separate contact 202, are connected electrically connected together so that at least two signal lines are electrically connected to each contact 204. Utilizing these methods, any number of data lines 64 may be connected to each single read out channel 74 and any number of scan lines 68 may be connected to each single driver channel 72. In yet another embodiment, the resolution of system 10 is altered by connecting a plurality of detector array lines together by electrically connecting a plurality of contacts 80 within detector array 12. Similarly, a plurality of driver channels 72 or read out channels 74 may be electrically connected together to reduce the resolution of system 10.

The above described flexible interconnect circuit allows the resolution of system 10 to be altered to meet the specific diagnostic imaging requirements while utilizing a single configuration detector array 12 and DAS 32. As a result, development, test, manufacturing and support costs are reduced.

The above described imaging system minimizes the number of components which must be changed to alter the resolution of the system. In addition, the above described flexible interconnect cable enables the resolution of the imaging system to be quickly and inexpensively modified.

While the invention has been described in terms of various specific embodiments, those skilled in the art will recognize that the invention can be practiced with modification within the spirit and scope of the claims. In addition to use with x-ray imaging systems, the system described herein may be used with other types of imaging systems, including, for example, computed tomography.

What is claimed is:

1. A flexible interconnect circuit for an imaging system, the imaging system including a detector array and at least one data acquisition system (DAS) module, the detector array having a plurality of signal lines, each DAS module having a plurality of channels, said flexible interconnect circuit configured to alter a resolution of the imaging system.

2. A flexible interconnect circuit in accordance with claim 1 wherein said flexible interconnect circuit comprises:
   a plurality of first end contacts;
   a plurality of second end contacts; and
   a plurality of conductors, each conductor electrically connected to at least one first end contact and at least one second end contact.

3. A flexible interconnect circuit in accordance with claim 1 wherein said flexible interconnect circuit comprises:
   a plurality of first end contacts;
   a plurality of second end contacts; and
   a plurality of conductors, each conductor electrically connected to a plurality of first end contact and at least one second end contact.

4. A flexible interconnect circuit in accordance with claim 1 wherein to alter a resolution of the imaging system said flexible interconnect circuit is configured to electrically connect a plurality of detector array signal lines to each DAS module channel.

5. A flexible interconnect circuit in accordance with claim 4 wherein the detector array includes M data signal lines and N scan signal lines and each DAS module includes at least one of a plurality of driver channels and a plurality of read out channels.

6. A flexible interconnect circuit in accordance with claim 5 wherein to electrically connect a plurality of detector array signal lines to each DAS module channel, said flexible interconnect circuit is configured to electrically connect a plurality of scan signal lines to each DAS module driver channel.

7. A flexible interconnect circuit in accordance with claim 6 wherein each first end contact is configured to electrically connect a plurality of scan signal lines to each conductor.

8. A flexible interconnect circuit in accordance with claim 6 wherein to electrically connect a plurality of scan signal lines to each DAS module driver channel, said flexible interconnect circuit is configured to electrically connect T scan lines to each DAS module driver channel.

9. A flexible interconnect circuit in accordance with claim 8 wherein said imaging system resolution is reduced to M by N/T.

10. A flexible interconnect circuit in accordance with claim 6 wherein to electrically connect a plurality of scan signal lines to each DAS module driver channel, said flexible interconnect circuit is configured to electrically connect two scan lines to each DAS module driver channel.

11. A flexible interconnect circuit in accordance with claim 10 wherein said imaging system resolution is reduced to M by N/2.

12. A flexible interconnect circuit in accordance with claim 5 wherein to electrically connect a plurality of detector array signal lines to each DAS module channel, said flexible interconnect circuit configured to electrically connect a plurality of data signal lines to each DAS module read out channel.

13. A flexible interconnect circuit in accordance with claim 12 wherein each first end contact is configured to be electrically connect a plurality of data signal lines to each conductor.

14. A flexible interconnect circuit in accordance with claim 12 wherein to electrically connect a plurality of data signal lines to each DAS module read out channel, said flexible interconnect circuit is configured to electrically connect V data signal lines to each DAS module read out channel.

15. A flexible interconnect circuit in accordance with claim 14 wherein said imaging system resolution is reduced to M/V by N.

16. A flexible interconnect circuit in accordance with claim 12 wherein to electrically connect a plurality of data signal lines to each DAS module read out channel, said flexible interconnect circuit is configured to electrically connect two data signal lines to each DAS module read out channel.

17. A flexible interconnect circuit in accordance with claim 16 wherein said imaging system resolution is reduced to M/2 by N.

18. A flexible interconnect circuit in accordance with claim 1 wherein the detector array is a solid state detector array.

19. A method for altering the resolution of an imaging system, the imaging system including a detector array having a plurality of signal lines, at least one data acquisition system (DAS) module and at least one flexible interconnect circuit, each DAS module having a plurality of channels, each flexible interconnect circuit having a plurality of first end contacts, a plurality of second end contacts and a plurality of conductors, each conductor electrically connected to a plurality of first end contacts and at least one second end contact, said method comprising the steps of:

determining a resolution of the imaging system, and electrically connecting the DAS module and the detector array utilizing at least one flexible interconnect circuit so that a plurality of detector array signal lines are electrically connected to each DAS module channel.

20. A method in accordance with claim 19 wherein each DAS module includes a plurality of contacts, each DAS module contact being electrically connected to a DAS module channel, and the detector array includes a plurality of contacts, each detector array contact electrically connected to a detector array signal line, and wherein electrically connecting the DAS module and the detector array utilizing at least one flexible interconnect circuit, said method comprising the steps of:

electrically connecting of a flexible interconnect circuit first end to the detector array so that each flexible interconnect circuit conductor is electrically connected to a plurality of detector array contacts; and electrically connecting of the flexible interconnect circuit second end to the DAS module so that each flexible interconnect circuit contact is electrically connected to at least one DAS module contact.

21. A method in accordance with claim 20 wherein each flexible interconnect circuit first end contact is configured to be electrically connected to plurality of detector array contacts.

22. A method in accordance with claim 19 wherein the detector array includes M data signal lines and N scan signal lines and each DAS module includes at least one of a plurality of driver channels and a plurality of read out channels.

23. A method in accordance with claim 20 wherein electrically connecting the DAS module and the detector array utilizing at least one flexible interconnect circuit comprises the step of electrically connecting a plurality of scan lines to each DAS module driver channel.

24. A method in accordance with claim 23 wherein electrically connecting a plurality of scan lines to each DAS module driver channel comprises the step of electrically connecting T scan lines to each DAS module driver channel so that the imaging system resolution is reduced to M by N/T.

25. A method in accordance with claim 23 wherein electrically connecting a plurality of scan lines to each DAS module driver channel comprises the step of electrically connecting two scan lines to each DAS module driver channel so that the imaging system resolution is reduced to M by N/2.

26. A method in accordance with claim 20 wherein electrically connecting the DAS module and the detector array utilizing at least one flexible interconnect circuit comprises the step of electrically connecting a plurality of data signal lines to each DAS module read out channel.

27. A method in accordance with claim 26 wherein electrically connecting a plurality of data signal lines to each DAS module read out channel comprises the step of electrically connecting V data signal lines to each DAS module read out channel so that the imaging system resolution is reduced to M/V by N.

28. A method in accordance with claim 26 wherein electrically connecting a plurality of data signal lines to each DAS module read out channel, comprises the step of electrically connecting four data signal lines to each DAS module read out channel so that the imaging system resolution is reduced to M/4 by N.

29. A method in accordance with claim 19 wherein the detector array is a solid state detector array.

* * * * *